United States Patent
Diaz et al.

(10) Patent No.: US 9,956,072 B2
(45) Date of Patent: May 1, 2018

(54) SURGICAL TEMPLATE AND DELIVERY DEVICE

(71) Applicant: LifeCell Corporation, Branchburg, NJ (US)

(72) Inventors: Michael Diaz, Satellite Beach, FL (US); Aaron Barere, Hoboken, NJ (US); Evan Friedman, Montvale, NJ (US); Sangwook Park, Dunellen, NJ (US); Heather Ansorge, New Hope, PA (US); Courtney Guyer, Hoboken, NJ (US)

(73) Assignee: LifeCell Corporation, Branchburg, NJ (US)

(*) Notice: Subject to any disclaimer, the term of this patent is extended or adjusted under 35 U.S.C. 154(b) by 27 days.

(21) Appl. No.: 13/804,741

(22) Filed: Mar. 14, 2013

(65) Prior Publication Data

US 2014/0100655 A1  Apr. 10, 2014

Related U.S. Application Data

(60) Provisional application No. 61/709,692, filed on Oct. 4, 2012.

(51) Int. Cl.
*A61F 2/12* (2006.01)
*A61B 90/00* (2016.01)

(52) U.S. Cl.
CPC ............. *A61F 2/12* (2013.01); *A61B 90/02* (2016.02); *A61L 2430/04* (2013.01); *F04C 2270/0421* (2013.01)

(58) Field of Classification Search
CPC .......................................... A61F 2/12
USPC ............................................................. 623/8
See application file for complete search history.

(56) References Cited

U.S. PATENT DOCUMENTS

| 3,446,213 A | * | 5/1969 | Goldman | ................. A41C 3/10 450/39 |
| 3,902,198 A | | 9/1975 | Rathjen | |
| 4,298,998 A | | 11/1981 | Naficy | |
| 4,840,629 A | | 6/1989 | Bustos | |
| 4,859,890 A | * | 8/1989 | Sedgewick | ................... 310/208 |
| 4,936,858 A | | 6/1990 | O'Keeffe | |
| 4,950,292 A | | 8/1990 | Audretsch | |
| 5,356,429 A | | 10/1994 | Seare | |
| 5,584,884 A | | 12/1996 | Pignataro | |
| 5,658,330 A | | 8/1997 | Carlisle et al. | |

(Continued)

FOREIGN PATENT DOCUMENTS

WO  2004/096098 A1  11/2004
WO  2006115892 A2  11/2006

(Continued)

OTHER PUBLICATIONS

"Kumihimo Disk, Plate, Instructions, Kits and E-Z Bob Bobbins" website; http://www.braidershand.com/disk.html Jan. 3, 2011.*

(Continued)

*Primary Examiner* — David H Willse
*Assistant Examiner* — Javier Blanco
(74) *Attorney, Agent, or Firm* — McCarter & English, LLP (57) ABSTRACT

The present disclosure provides devices and methods relating to surgical breast procedures. The devices can include a holder and backing to assist in positioning a biological material adjacent to a tissue expander or implant.

5 Claims, 12 Drawing Sheets

(56) References Cited

U.S. PATENT DOCUMENTS

| | | |
|---|---|---|
| 5,713,959 A | 2/1998 | Bartlett et al. |
| 5,954,767 A | 9/1999 | Pajotin et al. |
| 5,968,096 A | 10/1999 | Whitson et al. |
| 5,997,575 A | 12/1999 | Whitson et al. |
| 6,099,566 A | 8/2000 | Vonderharr et al. |
| 6,203,570 B1 | 3/2001 | Baeke |
| 6,210,439 B1 | 4/2001 | Firmin et al. |
| 6,368,541 B1 | 4/2002 | Pajotin et al. |
| 6,638,308 B2 | 10/2003 | Corbitt, Jr. et al. |
| 6,723,133 B1 | 4/2004 | Pajotin |
| 6,736,854 B2 | 5/2004 | Vadurro et al. |
| 6,740,122 B1 | 5/2004 | Pajotin |
| 7,011,688 B2 | 3/2006 | Gryska et al. |
| 7,476,249 B2 | 1/2009 | Frank |
| 7,547,322 B2 * | 6/2009 | Sarac ............... A61F 2/2415 623/1.24 |
| 9,114,003 B2 | 8/2015 | Kalus |
| 2001/0041936 A1 | 11/2001 | Corbitt et al. |
| 2002/0103542 A1 | 8/2002 | Bilbo |
| 2003/0212461 A1 | 11/2003 | Vadurro et al. |
| 2003/0212462 A1 | 11/2003 | Gryska et al. |
| 2004/0049269 A1 | 3/2004 | Corbitt et al. |
| 2004/0181227 A1 * | 9/2004 | Khalili ............... 606/69 |
| 2005/0021141 A1 | 1/2005 | Bleyer et al. |
| 2005/0165425 A1 | 7/2005 | Croce et al. |
| 2005/0187624 A1 | 8/2005 | Corbitt |
| 2005/0250977 A1 | 11/2005 | Montpetit et al. |
| 2005/0260176 A1 | 11/2005 | Ayares et al. |
| 2006/0030939 A1 | 2/2006 | Frank |
| 2006/0167338 A1 | 7/2006 | Shfaram |
| 2007/0038299 A1 | 2/2007 | Stone et al. |
| 2007/0088434 A1 | 4/2007 | Frank |
| 2007/0116678 A1 | 5/2007 | Sung et al. |
| 2007/0250177 A1 | 10/2007 | Bilbo |
| 2008/0027273 A1 | 1/2008 | Gutterman |
| 2008/0082113 A1 | 4/2008 | Bishop et al. |
| 2008/0097601 A1 | 4/2008 | Codori-Hurff et al. |
| 2008/0108134 A1 | 5/2008 | Murphy et al. |
| 2008/0167729 A1 | 7/2008 | Nelson et al. |
| 2008/0260853 A1 | 10/2008 | Firestone |
| 2008/0281418 A1 | 11/2008 | Firestone |
| 2008/0281419 A1 | 11/2008 | Matheny et al. |
| 2009/0024228 A1 | 1/2009 | Lesh |
| 2009/0082864 A1 * | 3/2009 | Chen ............... A61F 2/12 623/8 |
| 2009/0125107 A1 * | 5/2009 | Maxwell ............... 623/8 |
| 2011/0022171 A1 * | 1/2011 | Richter ............... A61F 2/12 623/8 |
| 2012/0010706 A1 | 1/2012 | Schuessler |
| 2012/0216887 A1 * | 8/2012 | Fagerlund et al. ........... 137/560 |
| 2012/0283826 A1 * | 11/2012 | Moses ............... A61F 2/12 623/8 |

FOREIGN PATENT DOCUMENTS

| | | | |
|---|---|---|---|
| WO | 2006/135998 A2 | 12/2006 | |
| WO | 2007004214 A2 | 1/2007 | |
| WO | WO 2007004214 A2 * | 1/2007 | ............... A61F 2/12 |
| WO | 2008/016919 A2 | 2/2008 | |
| WO | 2009/001293 A1 | 12/2008 | |
| WO | PCT/US2013/031324 | 3/2014 | |

OTHER PUBLICATIONS

Baxter, R. A., "Intracapsular allogenic dermal grafts for breast implant-related problems," Plast. Reconstr. Surg. 112(6): 1692-1696 (2003).

Breuing K.H. et al., "Immediate bilateral breast reconstruction with implants and inferolateral alloderm slings," Annals of Plastic Surgery 55(3): 232-239 (2005).

Breuing K.H. et al., "Inferolateral Alloderm Hammock for Implant Coverage in Breast Reconstruction," Annals of Plastic Surgery 59 (3): 250-255 (2007).

Colwell, A. S., et al., "Improving Shape and Symmetry in Mastopexy with Autologous or Cadaveric Dermal Slings," Annals of Plastic Surgery 61 (2): 138-142 (2008).

Darcy, C. M., "A Technique for Preparing Meshed Skin Grafts with Planned Expansion Ratios," British Journal of Plastic Surgery 56(1): 77-79 (2003).

Duncan, D. I., "Correction of Implant Rippling Using Allograft dermis," Aesthetic Surgery Journal 21 (1): 81-84 (2001).

Gamboa-Bobadilla, G. M., "Implant Breast Reconstruction Using Acellular Dermal Matrix," Annals fo Plastic Surgery 56 (1): 22-25 (2006).

Goes, J.C.S., "Periareolar Mammaplasty: Double Skin Technique with Application of Polyglactine or Mixed Mesh," Plastic and Reconstructive Surgery, Apr. 1996.

Goes, J.C.S., "Periareolar Mastopexy and Reduction with Mesh Support, Double Skin Technique," Surgery of the Breast: Principles and Art, 697, Apr. 1996.

International Search Report and Written Opinion for PCT/US2013/031324 dated Jul. 23, 2013.

International Search Report and Written Opinion on International Application PCT/US2010/042575 dated Jan. 14, 2011.

Salzberg, C. A., "Nonexpansive Immediate Breast Reconstruction Using Human Acellular Tissue Matrix Graft (Alloderm)," Annals of Plastic Suregery 57 (1) : 1-5 (2006).

Topol, B.M. et al., "Immediate Single-Stage Breast Reconstruction Using Implants and Human Acellular Dermal Tissue Matrix with Adjustment of the Lower Pole of the Breast to Reduce Unwanted Lift," Annals of Plastic Surgery 61 (5): 494-499 (2008).

Zienowicz, R. J. et al., "Implant-Based Breast Reconstruction With Allograft", Plast. Reconstr. Surg. 120: 373-374 (2007).

Goes, J.C.S., "Periareolar Mammaplasty: Double Skin Technique with Application of Polyglactine 910 Mesh," Rev. Soc. Bras. Cir. Plast. Estet. Reconstr., 7 (1, 2, 3) (1992).

Goes, J.C.S., "Pariareolar Mastopexy: Double Skin Technique with Mesh Support," Aesthetic Surgery Journal (Mar./Apr. 2003).

International Preliminary Report on Patentability and Written Opinion for International Patent Application No. PCT/US2013/031324 dated Apr. 7, 2015.

* cited by examiner

SURGICAL TEMPLATE AND DELIVERY DEVICE

This application claims priority under 35 U.S.C. § 119 to U.S. Provisional Patent Application No. 61/709,692, filed on Oct. 4, 2012.

The present disclosure relates generally to devices for positioning a sample of biocompatible material during breast procedures, as well as methods for treating tissue sites with the device.

Surgical breast procedures can use a tissue expander or a breast implant and a sample of biocompatible material, which can provide support to surrounding tissue. Proper placement of the material can be difficult to achieve, but can be important to the outcome of a breast procedure. Accordingly, there is a need for devices to assist in the placement of such biocompatible materials during surgical breast procedures.

According to various embodiments, a device for surgical breast procedures is provided. The device can comprise a holding member comprising a proximal edge and a distal edge and a first side and a second side, wherein the proximal edge comprises a convex portion curving away from the distal edge and the distal edge further comprises a convex portion curving away from the proximal edge. The device can further comprise a backing member associated with the holding member and comprising a first dimension and a second dimension, and at least one fastener configured to be connected to the holding member proximate to the proximal edge and configured to hold a sample of biocompatible material in apposition to the first side of the holding member.

According to certain embodiments a system for facilitating breast surgery is provided. The system can comprise a sample of biocompatible material. The system can further comprise a holding member comprising a proximal edge and a distal edge and a first side and a second side, wherein the proximal edge comprises a convex portion curving away from the distal edge, and the distal edge further comprises a convex portion curving away from the proximal edge and at least one indentation positioned along the distal edge. The system can also comprise a backing member comprising a first dimension and a second dimension, and at least one fastener configured to hold the sample of biocompatible material in apposition to the first side of the holding member.

According to certain embodiments, a method for preparing a site within a breast is provided. The method can comprise creating a tissue pocket within or posterior to a breast; and positioning within the tissue pocket a template comprising a sample of biocompatible material comprising a proximal edge and a distal edge, a holding member comprising a proximal edge and a distal edge, and a backing member, wherein the proximal edge of the biocompatible material is detachably connected proximate to the proximal edge of the holding member and the backing member is detachably connected proximate to the distal edge of the holding member. The method can further comprise fastening the distal edge of the biocompatible material to tissue within or surrounding the tissue pocket; and removing the holding member and the backing member from the tissue pocket.

According to certain embodiments, a device is provided. The device can comprise a holding member comprising a proximal edge and a distal edge and a first side and a second side, wherein the proximal edge comprises a convex portion curving away from the distal edge and the distal edge further comprises a convex portion curving away from the proximal edge, wherein the distal edge of the holding member comprises multiple indentations positioned along the distal edge.

The device can further comprise at least one fastener configured to be connected to the holding member proximate to the proximal edge and configured to hold a sample of biocompatible material in apposition to the first side of the holding member.

According to certain embodiments, a system for treating tissue is provided. The system can comprise a sample of biocompatible material and a holding member. The holding member can comprise a proximal edge and a distal edge and a first side and a second side, wherein the proximal edge comprises a convex portion curving away from the distal edge and the distal edge further comprises a convex portion curving away from the proximal edge, wherein the distal edge of the holding member comprises multiple indentations positioned along the distal edge. The system can further comprise at least one fastener configured to be connected to the holding member proximate to the proximal edge and configured to hold a sample of biocompatible material in apposition to the first side of the holding member.

According to certain embodiments, a method for performing breast surgery is provided. The method can comprise creating a tissue pocket in a breast and inserting a holding member into the tissue pocket, wherein the holding member includes a sample of biocompatible material attached thereto. The method can further comprise contacting a portion of the breast with a distal edge of the holding member and fastening the sample of biocompatible material to tissue within the breast, wherein the sample of biocompatible material is attached to the holding member during fastening. The sample of biocompatible material can also be detached from the holding member, and the holding member can be removed from the tissue pocket

BRIEF DESCRIPTION OF THE DRAWINGS

Reference will now be made to exemplary embodiments, examples of which are illustrated in the accompanying drawings. Wherever possible, the same reference numbers will be used throughout the drawings to refer to the same or like parts. The drawings are not necessarily to scale.

DESCRIPTION OF EXEMPLARY EMBODIMENTS

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The present disclosure relates generally to devices for surgical breast procedures and systems and methods relating to such devices. The devices can be used for tissue augmentation, repair or regeneration of damaged tissue, and/or correction of tissue defects. As such, the device, systems, and methods discussed herein can be suitable for a wide range of surgical applications, such as, for example, aesthetic surgery, breast reconstruction, breast augmentation, breast enhancement, breast reduction, and revisionary breast surgeries.

The devices discussed herein generally assist in surgical procedures wherein a sample of biocompatible material can be implanted within a tissue pocket in a breast. A variety of synthetic or biologic materials can be used. In various embodiments, the materials are capable of being attached to or inserted into and/or fixed within the body for a prolonged period of time without undesirable local or systemic effects. As non-limiting examples, the materials can include medical-grade polymeric materials; autologous, allogenic, or cadaveric tissue; and/or biomatrices, such as acellular tissue matrices. As used herein, acellular tissue matrices refer to tissue-derived biomatrix structures that can be made from any of a wide range of collagen-containing tissues by removing all, or substantially all, viable cells and all detectable subcellular components and/or debris generated by killing cells. Suitable exemplary acellular tissue matrices include ALLODERM® and STRATTICE™, which are acellular human and dermal tissue matrices, respectively, and are produced by LIFECELL CORPORATION (Branchburg, N.J.).

The sample of biocompatible material can support a tissue expander or breast implant within a tissue pocket, such as a subcutaneous, subglandular, subfascial, or subpectoral tissue pocket. Correct placement of the material can be important to the success of the surgical procedure, and incorrect placement can result in undesirable aesthetic results and/or medial, lateral, or inferior displacement of a tissue expander or breast implant, which may require additional surgeries to correct the location of the inframammary, lateral, or medial folds. Correct placement of the material can be hindered by difficulties in handling of the biocompatible material, difficulties visualizing the placement of the material, and difficulties manipulating the material within the tissue pocket, as well as movement while fastening the material to the underlying tissue. By addressing any or all of these problems, the devices disclosed herein can make such surgical procedures more consistent, faster, and more reproducible.

Figure 1:
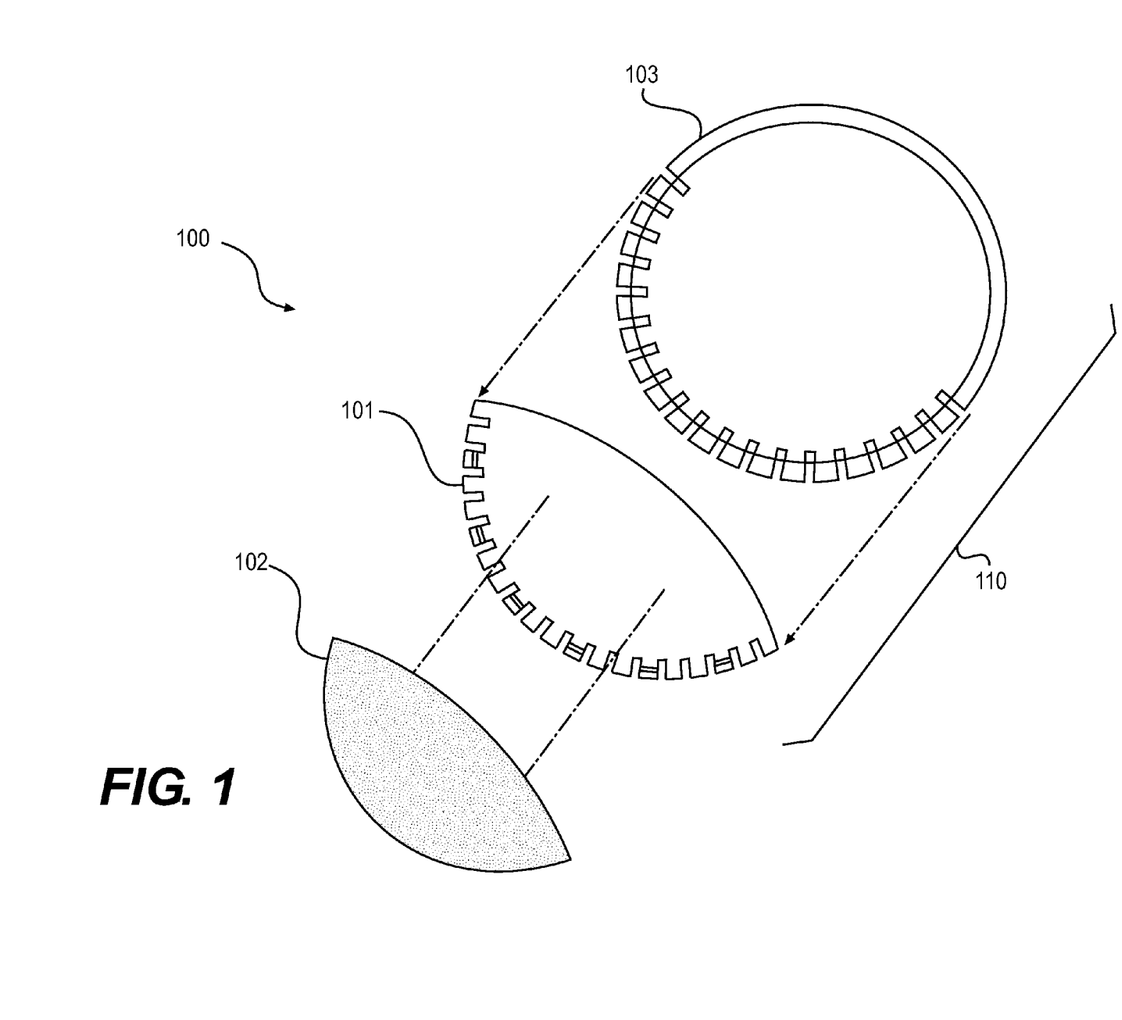
FIG. 1 is a perspective view of a system comprising a sample of biocompatible material and a device for surgical breast procedures, according to certain embodiments.

FIG. 1 is a perspective view of a system 100 comprising a sample of biocompatible material 102 and a device 110 for surgical breast procedures, according to certain embodiments. The system 100 can comprise a holding member 101 and a backing member 103. The sample of biocompatible material 102 can be attached to the holding member 101, and the holding member 101 can be attached to the backing member 103. The holding member 101 and/or backing member 103 can provide stiffness to the sample of biocompatible material, improving the ability of the surgeon to visualize and manipulate the sample of biocompatible material 102. The holding member 101 and the backing member 103 can together mimic the dimensions of the sample of biocompatible material 102 and a tissue expander or breast implant when placed in the tissue pocket. When correctly positioned and oriented within an implant site, the sample of biocompatible material 102 can be fastened to the underlying tissue. The device 110 can then be removed, leaving the sample of biocompatible material 102 fastened to the underlying tissue.

As described further below, the device 110 and system 100 can be used to position the sample of biocompatible material 102 at a desired location within a tissue expander and/or breast implant site. For example, in various embodiments, a holding member 101 can be shaped such that one edge (distal edge 203, shown in FIG. 2A), has a shape configured to produce a desired contour of a portion of the breast. For example, the distal edge 203 can be shaped to be positioned at or near a desired location for the inframammary fold (IMF), a medial border of the breast, a lateral border of the breast, or a location comprising parts of the IMF, medial border of the breast, and/or lateral border of the breast.

Figure 2A:
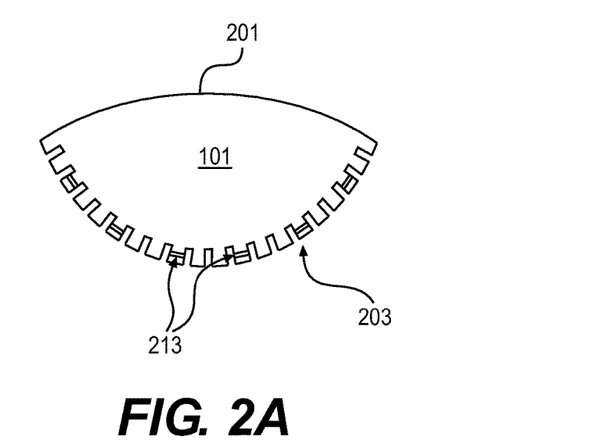
FIGS. 2A, 2B, and 2C are front, back, and side views, respectively, of a holding member for use in a device for surgical breast procedures, according to certain embodiments.
Figure 2B:
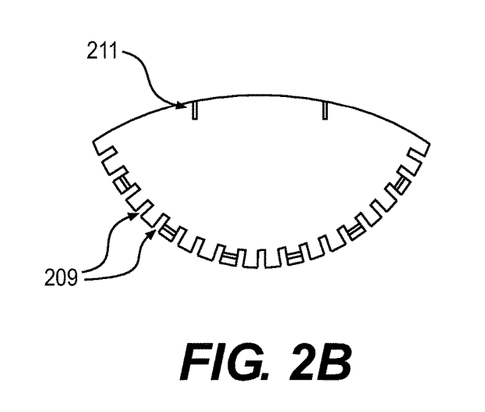
Figure 2C:
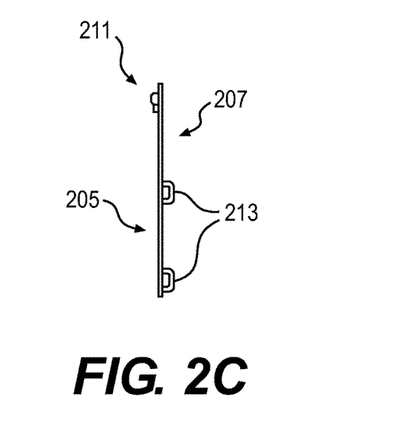

FIGS. 2A, 2B, and 2C are front, back, and side perspective views, respectively, of a holding member 101 for use in a device 110 for surgical breast procedures, according to certain embodiments. As shown in FIGS. 2A, 2B, and 2C, the holding member 101 can comprise a proximal edge 201 and a distal edge 203. A portion of the proximal edge 201 can be convex, curving away from the distal edge 203. Similarly, a portion of the distal edge 203 can be convex, curving away from the proximal edge 201. The proximal edge 201 and the distal edge 203 of the holding member 101 can both be convex, thus making the holding member 101 generally biconvex in shape. The holding member 101 can comprise a first side 205 and a second side 207. It will be appreciated that the proximal edge 201 and distal edge 203 may have variations in their shapes and may not be convex over their entire lengths. Furthermore, in some embodiments, at least one of the edges 201 and 203 can be substantially straight.

In some embodiments, the holding member 101 comprises at least one indentation 209. The at least one indentation 209 can be positioned along the distal edge 203 of the holding member 101 and can assist in fastening of the sample of biocompatible material 102 to tissue underlying the distal edge 203 of the holding member 101. The at least one indentation 209 can be sized to permit passage of a suture, a staple, or an effective quantity of adhesive or similar surgical fastener to fasten the biocompatible material 102 to the underlying tissue. The at least one indentation 209 can be a curved or polygonal recess or a slit in the distal edge 203. More than one indentation 209 can be present, and the indentations 209 can be regularly or irregularly sized, shaped, and/or spaced and can be distributed along either the entire distal edge 203 or one or more portions of the distal edge 203.

At least one fastener 211 can be configured to attach to and/or hold a sample of biocompatible material in apposition to the first side 205 of the holding member 101. In some embodiments, the fastener 211 can be attached to the holding member 101 proximate to the proximal edge 201, such that an edge of a sample of biocompatible material held in apposition to the first side 205 of the holding member 101 contacts the proximal edge 201 of the holding member 101. In some embodiments, the at least one fastener 211 can comprise multiple regularly spaced clips attached to the first side 205 of the holding member 101 and abutting the proximal edge 201 of the holding member 101. In some embodiments, the fastener 211 can be permanently attached to the first side 205 of the holding member 101. In other embodiments, the fastener 211 is removably attached to the holding member 101. Such fasteners can be used with any of the variations of the holding members described herein to hold a biocompatible material in apposition to the devices described herein.

At least one fastener 213 can be configured to attach to the backing member 103 and/or the holding member 101. The at least one fastener 213 can be configured to hold the backing member 103 in apposition to the second side 207 of the holding member 101. In some embodiments, the at least one fastener 213 can comprise multiple clips interspersed at regular or irregular intervals between multiple indentations 209. In some embodiments, the fasteners 213 can be permanently attached to the holding member 101 and/or backing member 103. In other embodiments, the fasteners 213 are removably attached to the holding member 101 and/or backing member 103. Such fasteners can be used with any of the variations of the holding members and backing members described.

Fasteners 211 and 213 can be chosen from a variety of different fasteners, for example mechanical fasteners, such as clips, pins, clasps, buttons, buckles, cleats, zippers, VEL-CRO®, hook and eye, toggle, screw, nail, suture, wire, ties, permanent or temporary magnets; or chemical fasteners such as adhesives, pastes, gums, cements, binders, and/or bonding agents.

The holding member 101, backing member 103, fastener 211, and fastener 213 can be associated with each other. As a non-limiting example, the holding member 101, backing member 103, fastener 211, and fastener 213 can be provided for use as part of a kit or a collection. They can be provided temporarily or permanently attached to one another and partially or completely assembled into the device 110. In some embodiments, the holding member 101 and backing member 103 are configured to be attachable and detachable multiple times. In some embodiments, the holding member 101 and backing member 103 are formed as a unitary structure, i.e., are formed as a single material and/or are permanently connected by an adhesive or other connection that does not permit easy separation of the components from one another. Further, any of the other devices and systems described herein can be provided as a collection or kit, as described in this paragraph.

Surgical breast procedures may require a variety of tissue expander and/or breast implant sizes. A particular breast implant or expander may require a certain tissue pocket size. Various disclosed embodiments include backing members 300, 400, 500, and 600 that are capable of mimicking tissue expanders or breast implants of various sizes and/or the base width of a tissue site, increasing the flexibility and utility of these embodiments. Furthermore, in certain embodiments, the backing members may be adjustable in size and/or shape, thereby allowing flexibility of use during a procedure.

Figure 3:
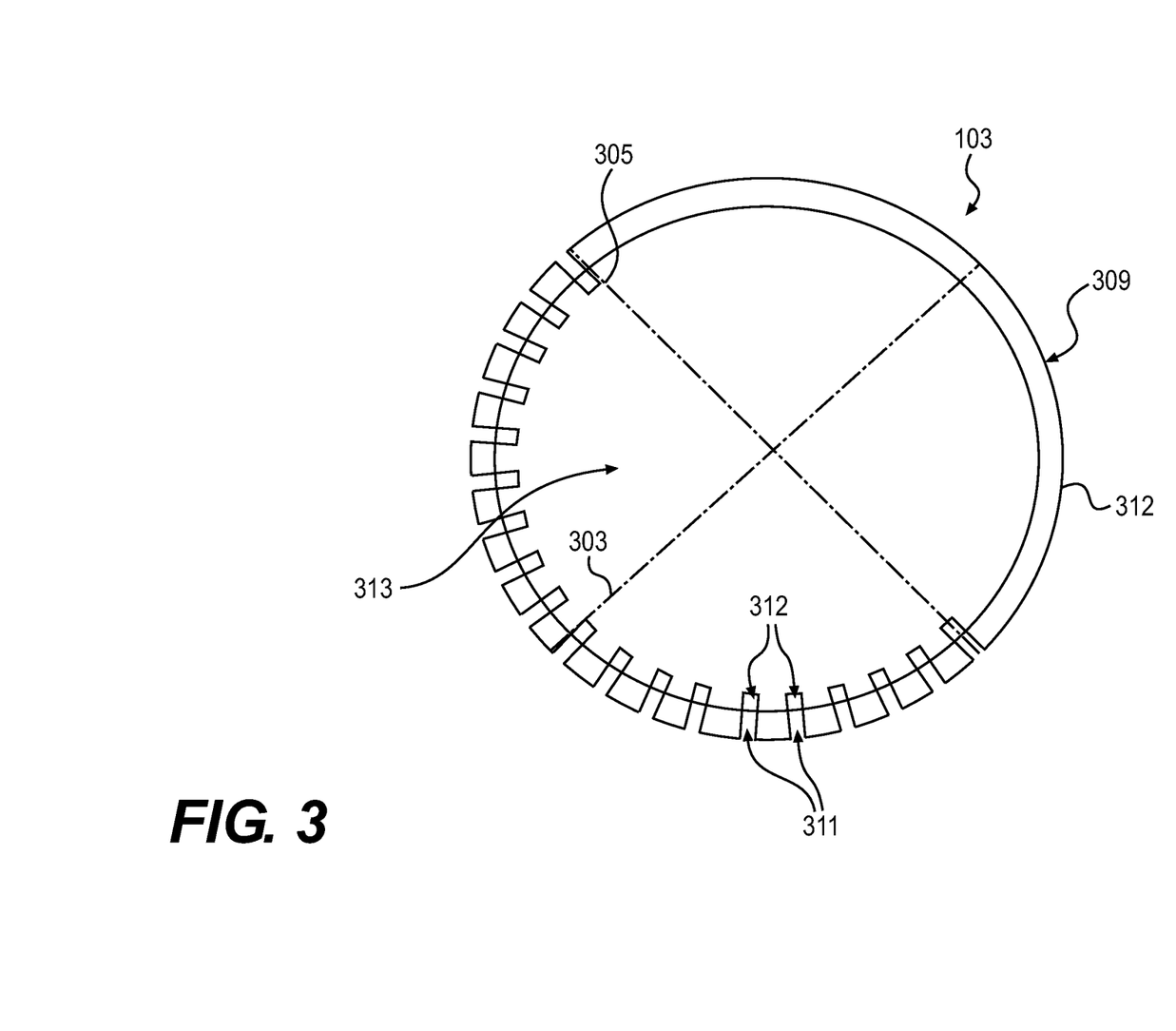
FIG. 3 is a top view of a backing member for use in a device for surgical breast procedures, according to certain embodiments.

FIG. 3 is a top view of the backing member 103 for use in a device 110 for surgical breast procedures, according to certain embodiments. The backing member 103 includes a first dimension 303 and a second dimension 305. In some embodiments, the first 303 and second dimensions 305 of the backing member 300 can approximate first and second dimensions of a tissue expander or breast implant. For example, the first and second dimensions of a tissue expander or breast implant can comprise a diameter of the tissue expander or a distance measured along a portion of the circumference of the tissue expander or implant, and the dimension 303 and 305 can correspond to those dimensions of the tissue expander or implant. As such, the backing member 103 can aid a surgeon in gauging the position of a biocompatible material 102 relative to the size of a desired expander or implant within a tissue pocket, as well as assist in gauging the size of an implant site relative to a desired expander or implant.

The backing member 103 can include a variety of different shapes and sizes. In some embodiments, the backing member 103 includes a disk shape. The disk shape can include a detachable outer ring member 309, along which at least one indentation 311 can be positioned, as well as an inner disk member 313. In other embodiments, the disk is formed of a unitary structure, i.e., without a detachable ring. The at least one indentation 311 can be sized to permit use of a suture, staple, or other fixation device to secure a biocompatible material to tissue. In some embodiments, the disk 103 comprises at least one indentation 311 positioned along the outer edge 312 of the detachable outer member (i.e., the detachable outer ring member 309) and extending into the inner disk member 313 (see inner extension 312). As such, a surgeon can modify the size of the backing member 103 during a procedure by removing or replacing the outer ring member 309. For example, the outer ring can have a diameter of about 12 cm, and the inner disk member 313 can have a diameter of about 11 cm. This embodiment permits a single backing member 103 to mimic more than one tissue expander. In various embodiments, the indentations 311 can have a position corresponding to the location of indentations 209 of the holding member 101.

Figure 4:
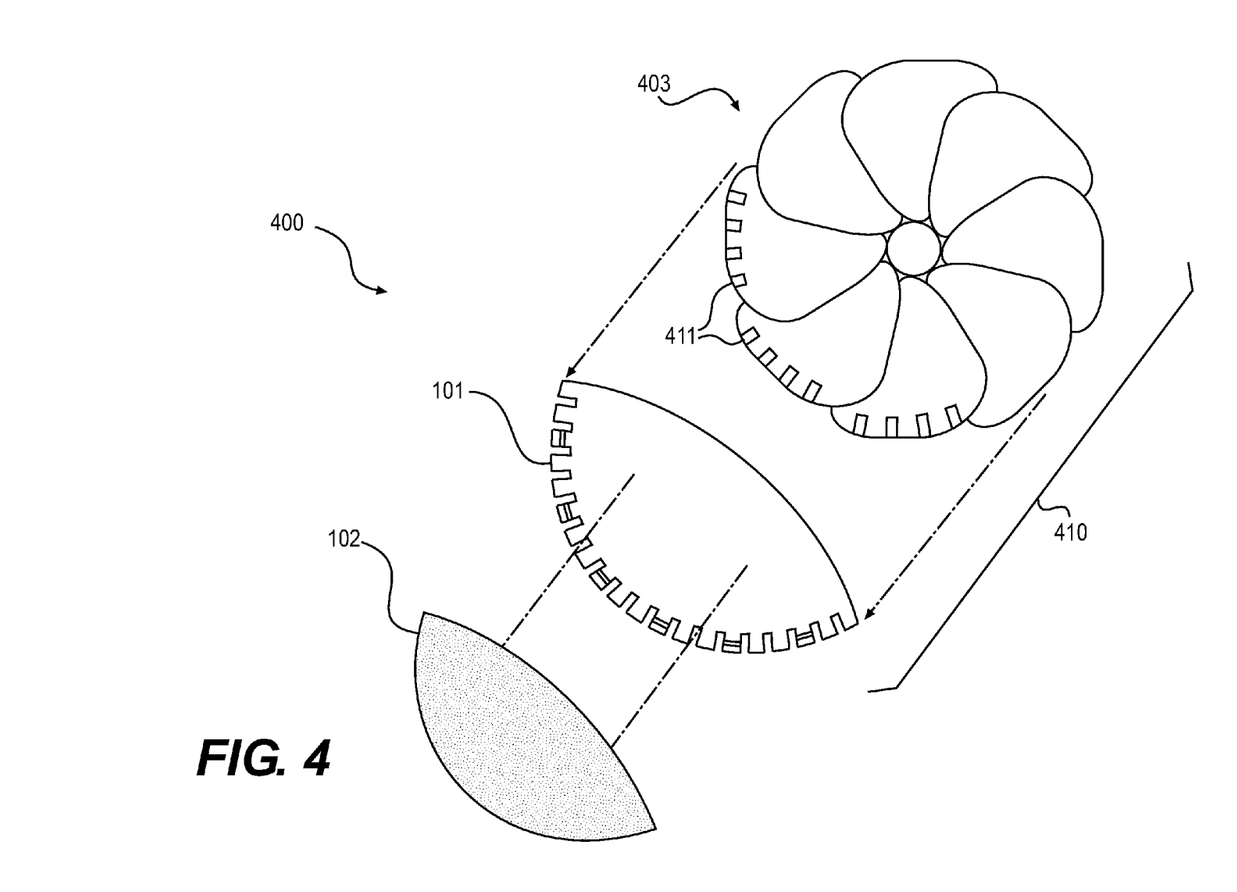
FIG. 4 is a perspective view of a system comprising a sample of biocompatible material and a device for surgical breast procedures, according to certain embodiments.

FIG. 4 is a perspective view of a system 400 comprising a sample of biocompatible material 102 and a device 410 for surgical breast procedures, according to certain embodiments. Similar to the system 100 of FIG. 1, the system 400 can comprise a holding member 101 and a backing member 403. A sample of biocompatible material 102 can be attached to the holding member 101, and the holding member 101 can be attached to the backing member 403. The holding member 101 and/or backing member 403 can provide stiffness to the sample of biocompatible material, improving the ability of the surgeon to visualize and manipulate the sample of biocompatible material 102. As noted above, however, the backing members discussed herein, can have a variety of shapes and configurations, and the structure of backing member 403 is described in more detail below.

Figure 5A:
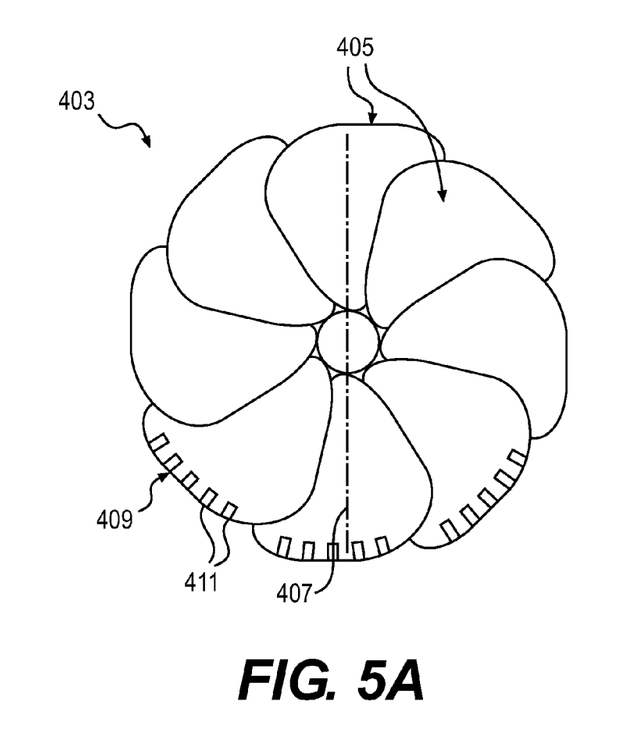
FIGS. 5A and 5B are front and rear views, respectively, of a backing member for use in a device for surgical breast procedures, according to certain embodiments.
Figure 5B:
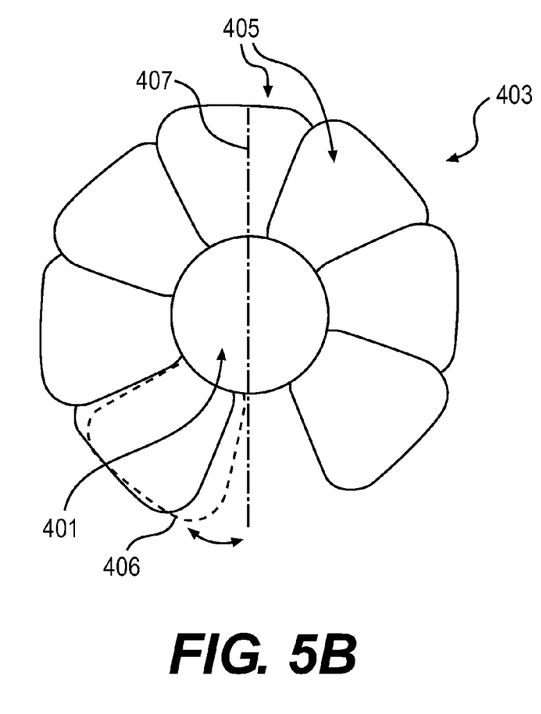

FIGS. 5A and 5B are front and rear views, respectively, of the backing member 403, according to certain embodiments. The backing member 403 comprises a central support member 401 adjustably connected to a plurality of vanes 405. The vanes 405 can be flat, with a top surface and a bottom surface, or can have some degree of curvature. The vanes 405 are distributed around the central support member 401, for example in a circular arrangement. These vanes 405 can circumferentially overlap to form a circular shape comprising a diameter 407 and an outside edge 409. In some embodiments, for example, each vane 405 in the circular formation has two adjacent vanes. In such embodiments, each vane 405 in the circular formation can be either above the two adjacent vanes, below the two adjacent vanes, or above one adjacent vane and below the other adjacent vane.

In some embodiments, the adjustable connection between the central support member 401 and each vane 405 permits that vane 405 to move with respect to the central support member 401, the movement having a circumferential component. For example, as shown in FIG. 5B, at least one vane 406 can be moved circumferentially to reduce the area of backing member 403. The circumferential component of this movement causes the outside circumference of the circular shape to increase or decrease and can affect the degree of circumferential overlap between the vanes 405. Each of the vanes 405 can have at least two ends, tapering from a broader end distal to the central support member to a narrower end proximal to the central support member.

As with the embodiment of FIG. 1, the device 410 can include one or more fasteners 213 that can be attached to the holding member 101 proximate to the distal edge 203 of the holding member 101 and/or to the backing member 403 to hold the holding member 101 and backing member 403 in apposition. In such embodiments, when the backing member 403 is held in apposition to the second side 207 of the holding member 101, the outside edge 409 can be held in contact with the distal edge 203 of the holding member 101.

The backing member 403 can further include one or more indentations 411. The indentations 411 can be positioned along at least one edge of the backing member 403 at a position corresponding to the position of indentations 209 on the holding member 101. The indentations can be spaced and oriented to align with indentations of a backing member.

Figure 6:
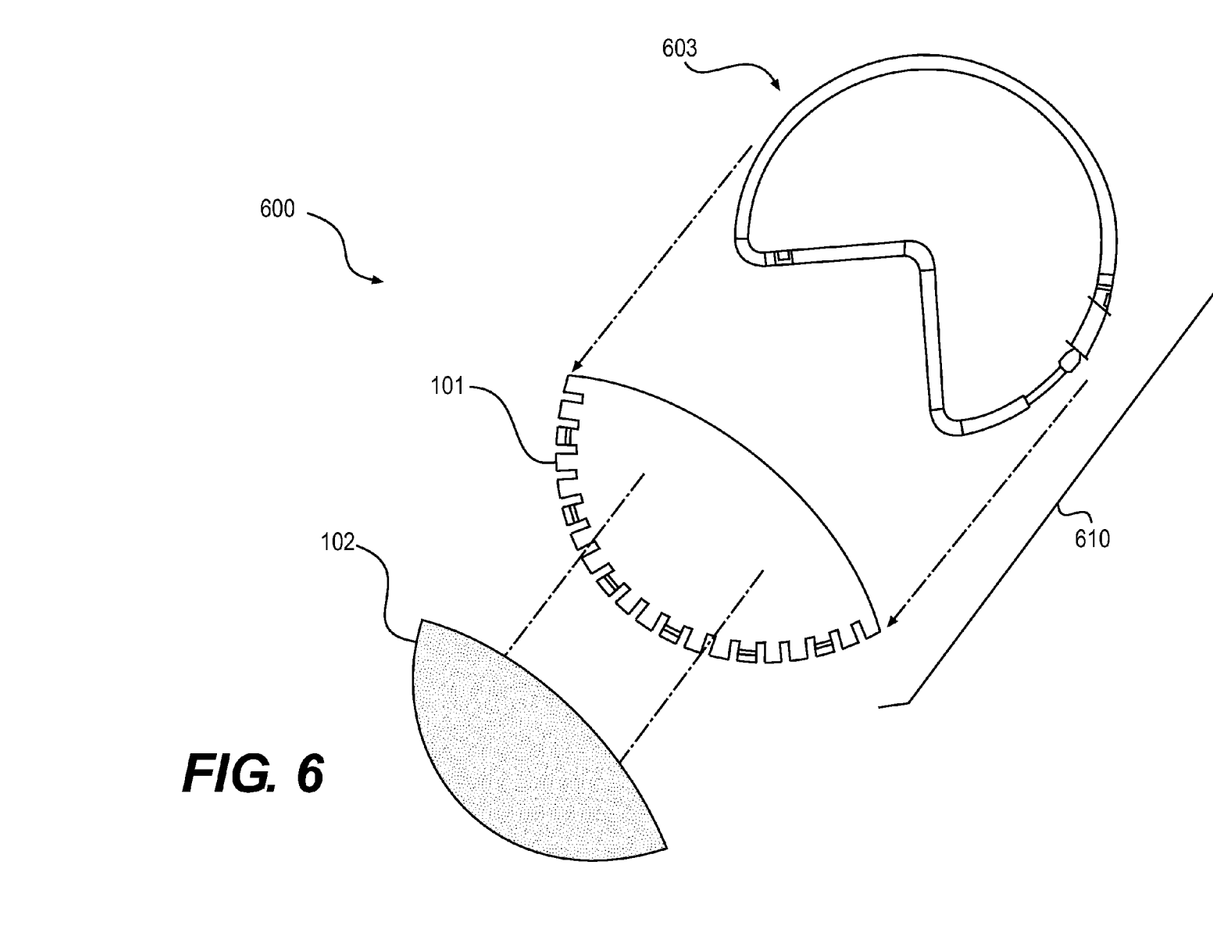
FIG. 6 is a perspective view of a system comprising a sample of biocompatible material and a device for surgical breast procedures, according to certain embodiments.

FIG. 6 is a perspective view of a system 600 comprising a sample of biocompatible material 102 and a device 610 for surgical breast procedures, according to certain embodiments. The system 600 is similar to the systems 100 and 400 described above, except that the backing member 603 of the device 610 has a different structure.

Figure 7:
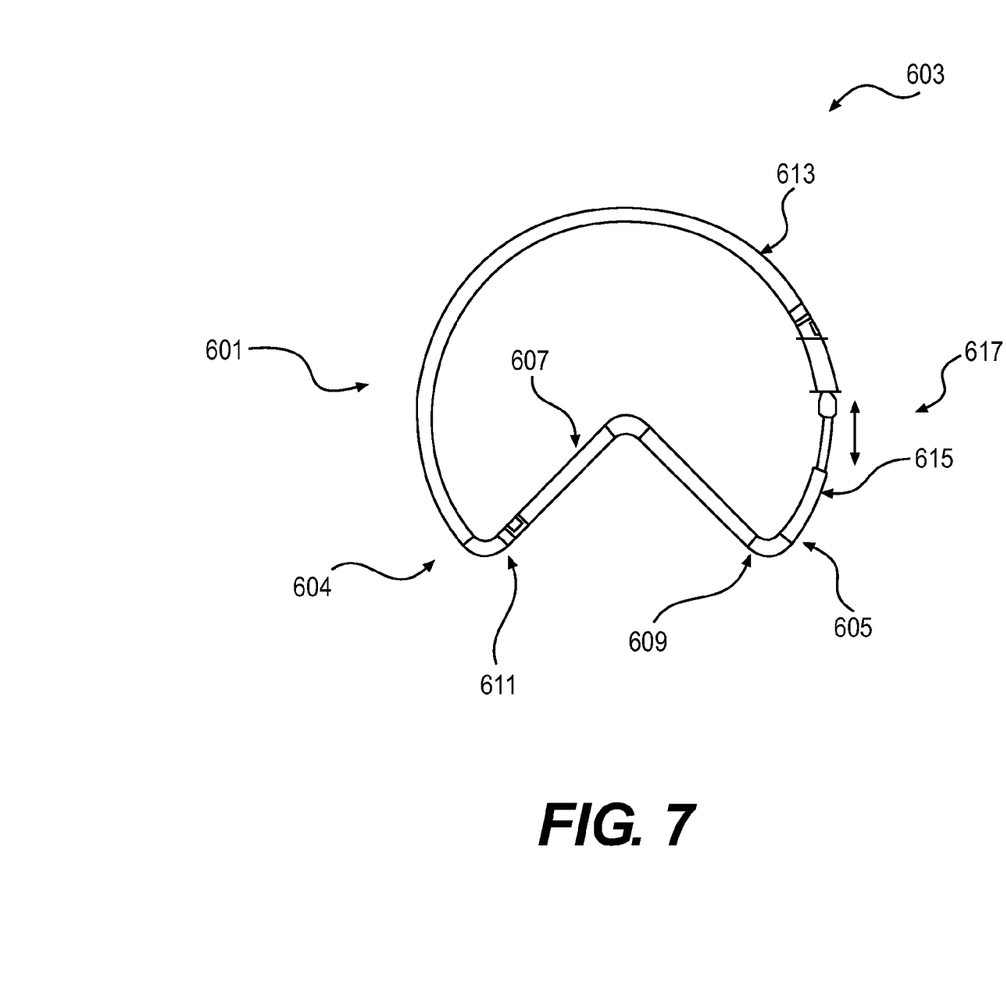
FIG. 7 is a perspective view of a backing member for use in a device for surgical breast procedures, according to certain embodiments.

FIG. 7 is a perspective view of the backing member 603 for use in a device for surgical breast procedures, according to certain embodiments. The backing member 603 comprises a curved segment 601 having a maximum length and a connecting segment 607. In some embodiments, portions of the curved segment 601 can be a circular arc having a first end 604 connected to a first end 611 of the connecting segment 607 and having a second end 605 connected to a second end 609 of the connecting segment 607. The width, thickness, and cross-sectional area of the curved segment 601 can vary, and the material dimensions and mechanical properties can be selected to produce a desired rigidity.

In some embodiments, the curved segment 601 can include a first interlocking section 613, a second interlocking section 615, and an adjustable connector 617 for adjusting the length of the curved segment by securing the first interlocking segment 613 to the second interlocking segment 615. In some embodiments, the first interlocking section 613 and the second interlocking section 615 can overlap to a varying degree determinable by the adjustable connector 617 for adjusting the length of the curved segment. By way of non-limiting example, the first interlocking section 613 can be hollow, and the second interlocking section 615 can fit at least partially within the first interlocking section 613. Similarly, the second interlocking section 615 can have a top face, the first interlocking section 613 can have a bottom face, and the first interlocking section 613 can contact the second interlocking section 615 face-to-face.

The adjustable connector 617 for adjusting the length of the curved segment can prevent unintentional changes in the overlap between the first interlocking section 613 and the second interlocking section 615, thus preventing unintentional alteration of the length of the curved segment 601. As shown in FIG. 7, for example, the adjustable connector 617 for adjusting the length of the curved segment can comprise a button projecting from the second interlocking section 615 through a slot in the first interlocking section 613. By projecting through the slot, the button restricts the relative movement of the first 613 and second 615 interlocking sections. Alternatively, other mechanisms can be used instead of a button.

In some embodiments, at least one fastener 213 (as depicted with respect to the backing member and holding members described above) can be attached to the holding member 101 proximate to the distal edge 203 of the holding member 101. In such embodiments, when the backing member 603 is held in apposition to the second side 207 of the holding member 101, a portion of the curved segment 601 can be held in contact with the distal edge of the holding member 101. Similarly, the at least one fastener 213 can hold a portion of the connecting segment 607 in contact with the distal edge of the holding member 101.

Figure 8A:
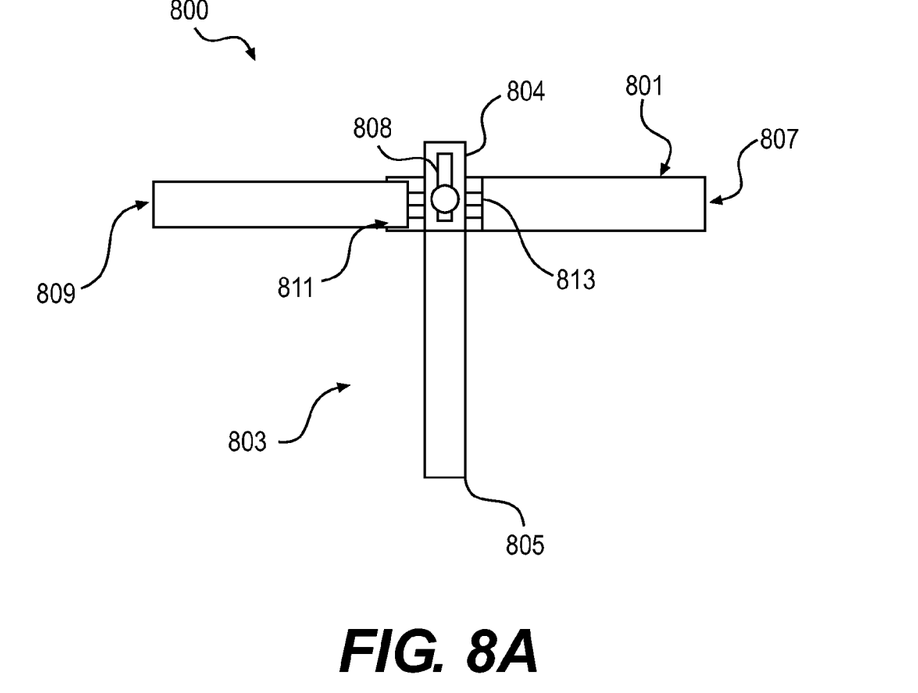
FIG. 8A is a rear view of a backing member for use in a device for surgical breast procedures, according to certain embodiments.
Figure 8B:
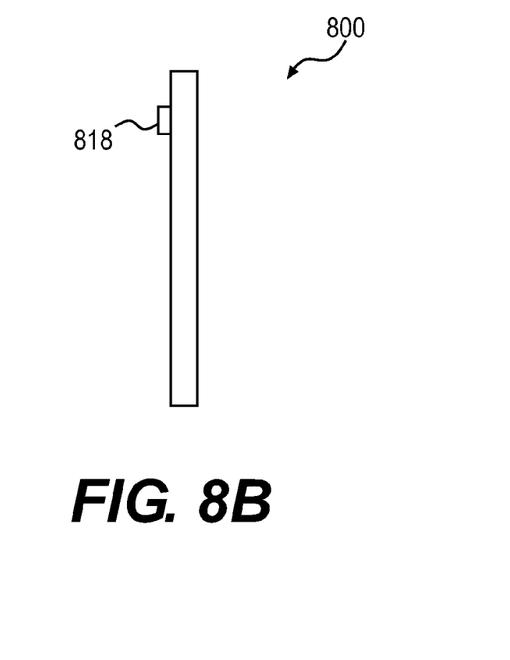
FIG. 8B is a side view of a backing member for use in a device for surgical breast procedures, according to certain embodiments.

FIG. 8A is a rear view of a backing member 800 for use in a device for surgical breast procedures, according to certain embodiments; and FIG. 8B is a side view of the device of FIG. 8A. The backing member 800 comprises a first overlapping member 801 having a first end 807 and a second end 809 and a second overlapping member 803 having a first end 804 and a second end 805. Each overlapping member can be thin, substantially flat, and substantially longer than it is wide. The first overlapping member 801 can overlap the first end 804 of the second overlapping member 803. An adjustable connector 808 can be provided to control the relative position and orientation of the two overlapping members 801, 803 and to connect the first overlapping member 801 and the second overlapping member 803. As shown in FIG. 8B, the device can include fasteners 818 for attachment to a holding member.

The adjustable connector 808 can prevent translation of either the first overlapping member 801 or the second overlapping member 803 perpendicular to a plane formed by the first overlapping member 801 and second overlapping member 803. The adjustable connector 808 can also permit limited translation of the first overlapping member 801 and the second overlapping member 803 with respect to each other and limited rotation around the point of intersection of the first overlapping member 801 and second overlapping member 803 in a plane formed by the first overlapping member 801 and second overlapping member 803. Each of the first overlapping member 801 and second overlapping member 803 can have a slot, indentation, or similar cut-out. Such slot, indentation, or similar cut-out can overlap, and the adjustable connector 808 can include a pin, dowel, threaded or unthreaded rod, screw, or similar connector inserted through the cut-outs in the first overlapping member 801 and second overlapping member 803. Such a connector can be secured at one or both ends with a cotter pin, nut, bolt, or similar locking mechanism such that the first overlapping member 801 and second overlapping member 803 are held in contact with variable force. The degree of force can be decreased to permit an intentional change in the respective position and orientation of the first overlapping member 801 and second overlapping member 803 and then increased to prevent unintentional changes in the respective position and orientation of the first overlapping member 801 and second overlapping member 803. In this manner, the position and the orientation of the first overlapping member 801 and second overlapping member 803 can be adjusted, enabling the backing member 800 to mimic the dimensions of the tissue expander.

In some embodiments, the first overlapping member 801 can further comprise a first interlocking member 811 and/or a second interlocking member 813. The interlocking members 811, 813 can allow adjustment of the length of the overlapping member 801. Each of the first interlocking member 811 and second interlocking member 813 can have a slot, indentation, or similar cut-out. Such cut-outs can overlap and a pin, dowel, threaded or unthreaded rod, screw, or similar connector can be inserted through said cut-outs. Such connector can be secured at one or both ends with a cotter pin, nut, bolt, or similar locking mechanism such that the first interlocking member 811 and second interlocking member 813 are held in contact with variable force. The length of the first overlapping member can be adjusted so that the backing member will mimic tissue expanders or implants of various sizes.

Figure 9A:
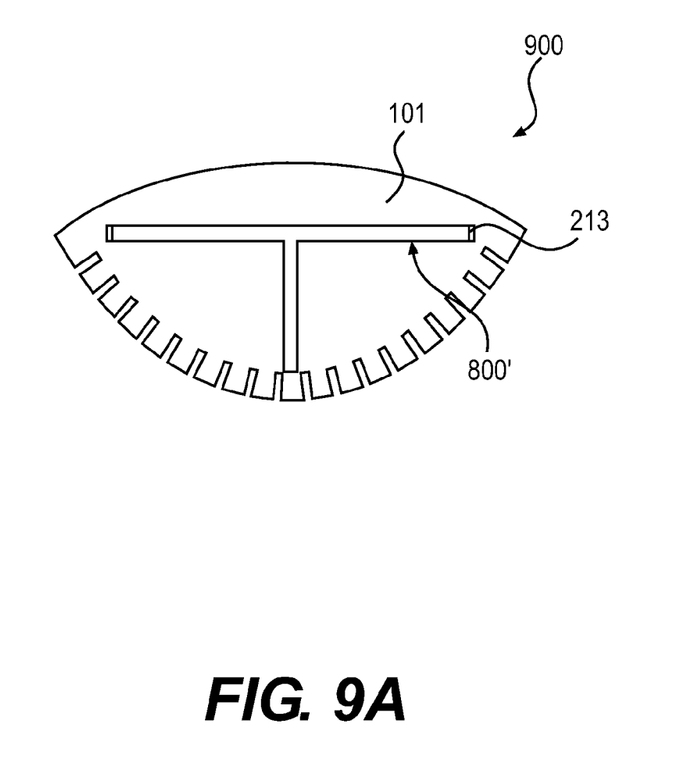
FIG. 9A is a rear view of a device for use in surgical breast procedures, according to certain embodiments.

FIG. 9A is a rear view of a device 900 for use in surgical breast procedures, according to certain embodiments. The device 900 comprises a holding member 101 and a backing member 800'. Backing member 800' can have a variety of configurations. In one embodiment, backing member 800' has a T-shape and can incorporate features, as described with respect to FIG. 8, but the backing member 800' can have a variety of different shapes.

In certain embodiments, the backing member 800' can be integrally formed as a part of or permanently connected to the holding member. For example, as shown in FIG. 9A, the backing member 800' can be permanently attached to the holding member 101 to provide desired rigidity to the holding member. The backing member 800 can be attached to the holding member using an adhesive and/or by embedding the backing member 800 within the holding member 101, e.g., by embedding within a polymeric material forming the backing member.

Figure 9B:
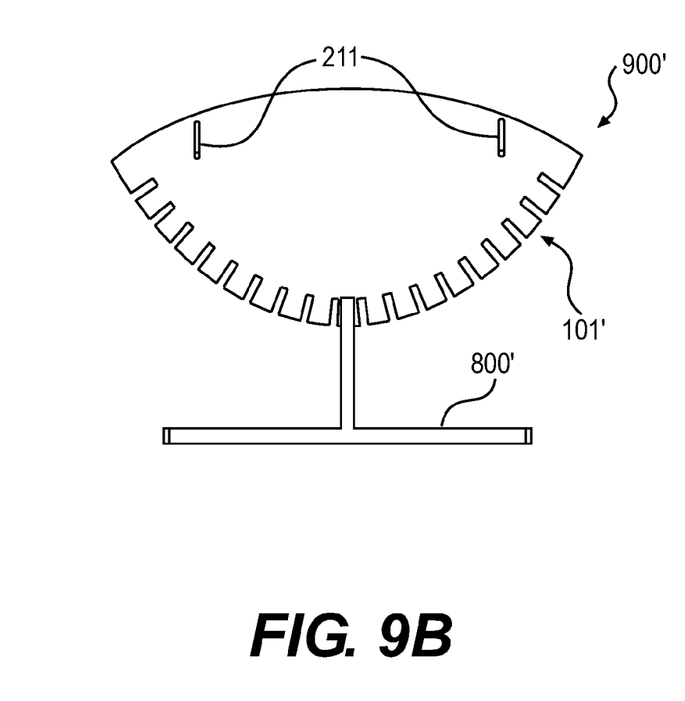
FIG. 9B is a front view of a device for use in surgical breast procedures, according to certain embodiments.

FIG. 9B is a front view of the device 900' for use in surgical breast procedures, according to certain embodiments, before final assembly. As shown, the backing member 800' can be formed of the same material as the holding member 101', or can be formed of another material attached to and extending from the holding member 101'. The backing member 800' can then be bent or folded and connected to the surface of the holding member. As with each of the devices described herein, the devices 900 and 900' can include fasteners 211 for removably attaching a biologic material to the device for implantation of the biologic material.

Figure 10:
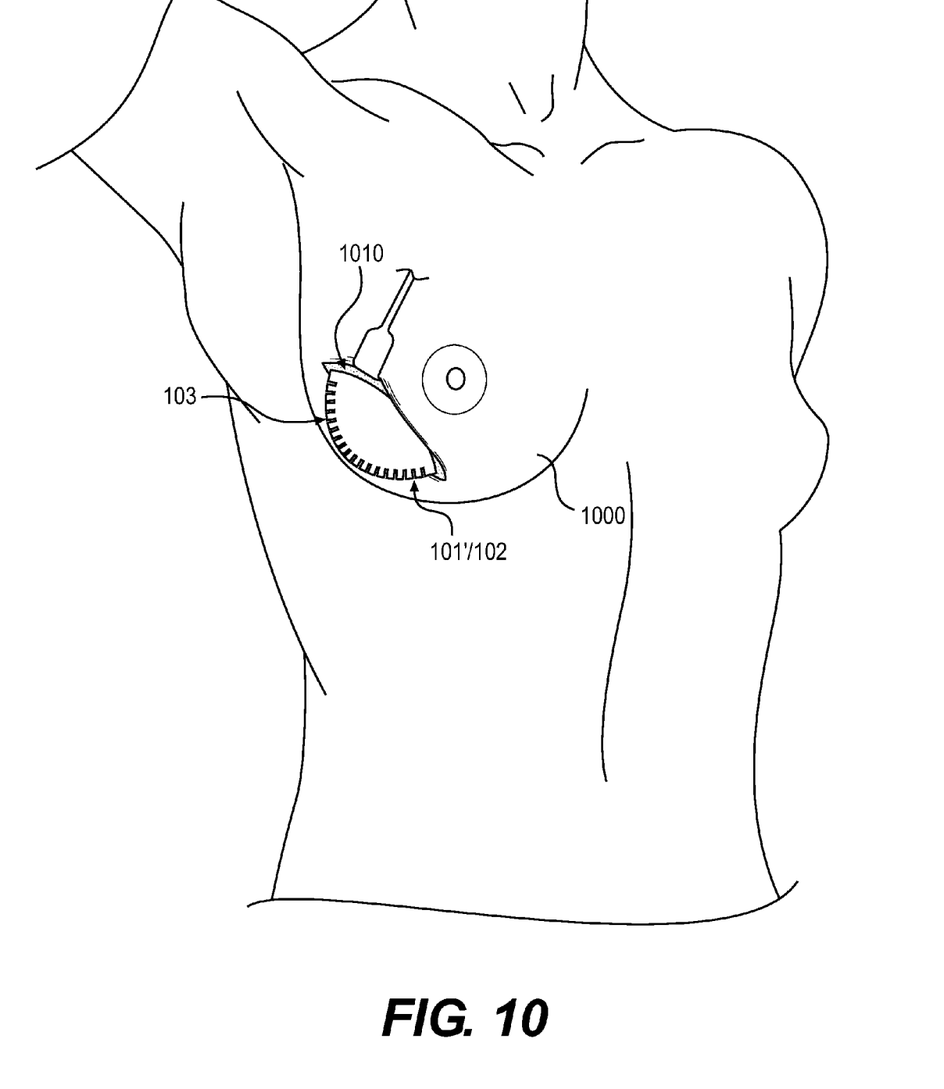
FIG. 10 illustrates use of a system for facilitating breast surgery, according to certain embodiments.

FIG. 10 illustrates use of a system for facilitating breast surgery, according to certain embodiments. In particular, FIG. 10 illustrates use of the system 900' of FIG. 9B. Any system described herein, however, may be similarly used as part of a method for facilitating breast surgery. The method for facilitating breast surgery may first include creating a tissue pocket in a breast. In one embodiment, for example, an incision can be made in the inframammary fold or other desired location near the breast 1000; the pectorialis muscle can then be released and raised; and a tissue pocket 1010 created partially or completely under the pectorialis muscle. Alternatively, the tissue pocket 1010 can be formed for placement of an implant anterior to the pectorialis muscle in a subcutaneous or subglandular pocket.

The method for facilitating breast surgery may further include selecting a system for facilitating the placement of biocompatible material 102 including a holding member and/or a backing member. As described herein, the holding member and the backing member may be fastened to one another. The holding member and the backing member may be selected so that when the holding member and the backing member are placed in the tissue pocket, they mimic the dimensions of a biological sample 102 and/or a tissue expander or implant. In addition, or alternatively, the holding member may be selected so that its distal edge 203 has a shape configured to produce a desired contour of a portion of the breast. In one embodiment, for example, a device operator may select a holding member and a backing member that each include a desired size and shape. Alternatively, or in addition, a device operator may adjust the size and shape of the holding member and/or backing member so that a desired size and shape may be achieved.

Prior to insertion of the holding member and backing member into the tissue pocket 1010, the method for facilitating breast surgery may include attaching a sample of biocompatible material 102 to the holding member. Attachment may include any suitable means described herein or known to those skilled in the art so long as the sample of biocompatible material 102 can be detached from the holding member upon placement in the created tissue pocket 1010.

The sample of biocompatible material 102 may be attached at any suitable location on the holding member, such that the sample of biocompatible material 102 can be placed in a desired position within the tissue pocket 1010. In one embodiment, as illustrated in FIGS. 1 and 2A-C, for example, the method may include attaching the sample of biocompatible material 102 with at least one fastener 211 proximate to the proximal edge 201 of the holding member 101, such that the sample of biocompatible material 102 is held in opposition to the first side 205 of holding member 101. The at least one fastener 211 may be any suitable fastener described herein or known to those skilled in the art, including, but not limited to a clip, suture, wire, tie, adhesive, paste, or gum.

Once the sample of biocompatible material 102 is attached to the holding member, the method for facilitating breast surgery can further include inserting the holding member, backing member and sample of biocompatible material 102 at any suitable location within the created tissue pocket 1010. For example, suitable locations within the created tissue pocket may include, but are not limited to a location at or near a desired location for the inframammary fold, medial border of the breast, and/or lateral border of the breast.

Upon placement of the holding member, backing member, and sample of biocompatible material 102 in a desired location within the created pocket, the sample of biocompatible material 102 may be fastened to underlying tissue in the breast. Fastening may be accomplished via any fastening means known to those skilled in the art including, but not limited to, a suture, a staple, and/or an effective quantity of adhesive. Fastening of the sample of biocompatible material 102 to the underlying tissue in the breast may occur while the sample of biocompatible material 102 is attached to the holding member. In one embodiment, for example, the fasteners may pass through at least one indentation 209 in the distal edge 203 of the holding member 101.

Once the sample of biocompatible material 102 is fastened to the underlying tissue in the breast at the desired location, the sample of biocompatible material 102 may be detached from the holding member, and the holding member and the backing member may be removed from the created tissue pocket 1010.

Figure 11:
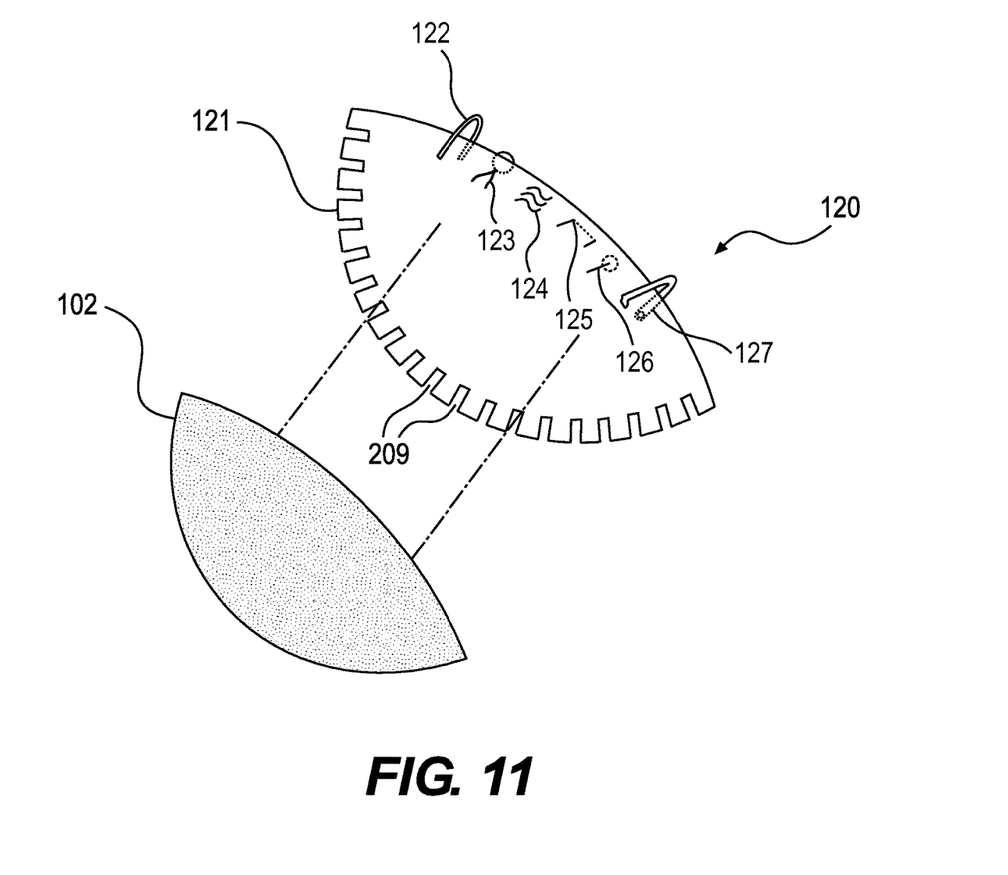
FIG. 11 is a perspective view of a system comprising a sample of biocompatible material and a device for surgical breast procedures, according to certain embodiments.

FIG. 11 is a perspective view of a system comprising a sample of biocompatible material 102 and a device 120 for surgical breast procedures, according to certain embodiments. As shown, the device 120 is a unitary structure. That is to say, the device includes a holding member 121, which has a shape similar to those described above (see element 101). In the embodiment of FIG. 11, however, the device does not include a separate backing member. Rather, the device 120 is formed of a material having desired flexibility/rigidity such that a separate backing member is not needed. The device 120 has indentations 209, which function like those described with reference to holding member 101.

Figure 12:
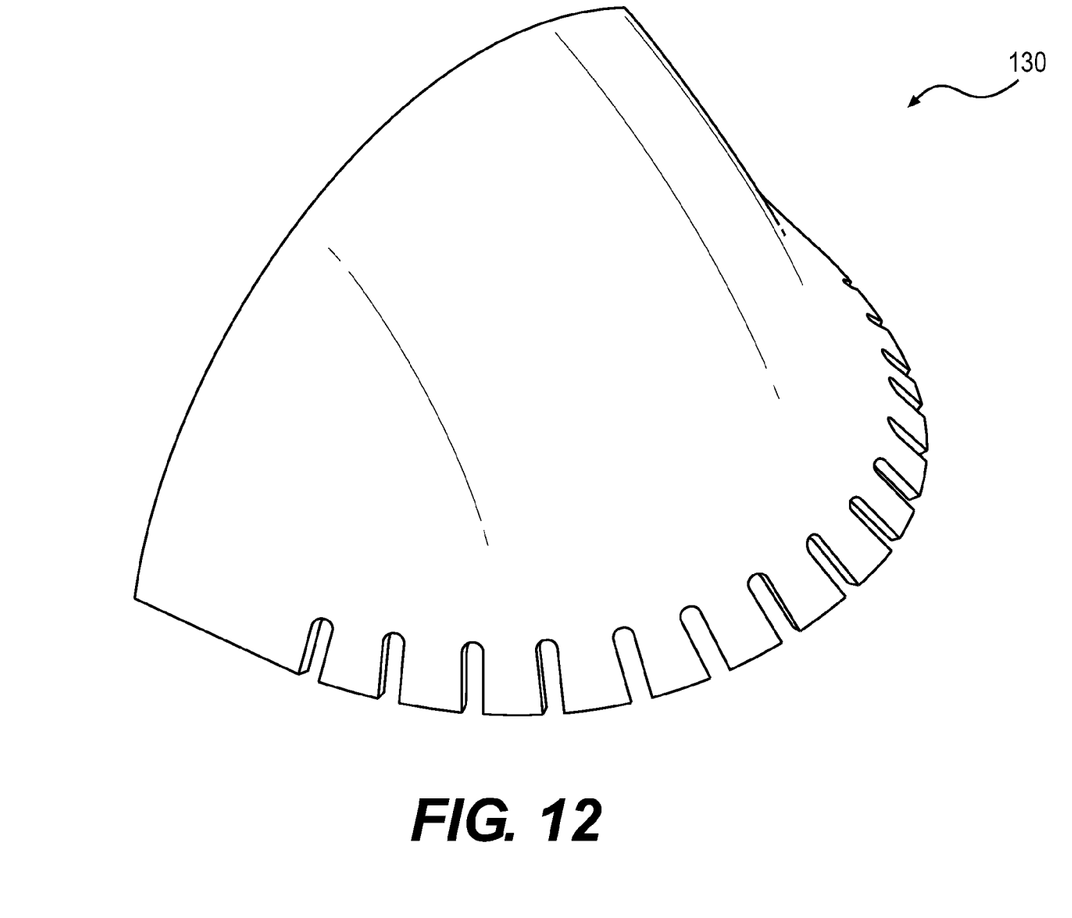
FIG. 12 is a perspective view of a device for surgical breast procedures, according to certain embodiments.

In each of the embodiments described above, the backing member and/or holding member are depicted as substantially flat objects. The devices can, however, have a number of suitable three-dimensional shapes. For example, FIG. 12 is a perspective view of a device for surgical breast procedures, according to certain embodiments. As shown, the device comprises a backing member 130 having a curved or cup-like configuration. The configuration may be selected to mimic an implant site and/or a tissue expander or implant. Further, a holding member may be configured to have a similar shape. In addition, the backing member may be formed of a flexible material, and the holding member can be provided in a range of suitable shapes to produce a desired shape for the backing member 130 at the time of use.

In addition, the holding members described herein, as well as the biocompatible materials for use therewith, can have any desired shape. For example, the holding member (with or without a backing member of similar or different shape) and/or biocompatible material can be rectangular, square, ovoid, triangular, trapezoidal, or any other shape. Such holding members can include a plurality of indentations along at least one edge to assist in fastening the biocompatible material to tissue.

Other embodiments will be apparent to those skilled in the art from consideration of the specification and practice of this disclosure. It is intended that the specification and examples be considered as exemplary only, with the true scope and spirit of the disclosed devices and methods being indicated by the following claims.

What is claimed is:

1. An implantable breast implant support and positioning device implantable within a tissue pocket in a breast, the device comprising:
   a disc-shaped backing member,
   a holding member formed of a stiff material shaped in a cup-like configuration comprising a proximal edge and a distal edge and a first side and a second side,
     wherein the proximal edge comprises a convex portion curving away from the distal edge, and the distal edge comprises a convex portion curving away from the proximal edge,
     wherein the convex portions of the proximal and distal edges extend an entire length of the holding member,
     wherein the convex portion of the proximal edge has a first radius of curvature and the convex portion of the distal edge has a second radius of curvature, the first radius of curvature being different from the second radius of curvature,
     wherein the distal edge of the holding member is configured to produce a desired contour,
     wherein the distal edge of the holding member comprises multiple adjacent indentations formed along the convex portion of the distal edge,
     wherein the multiple indentations are dimensioned to permit passage of a surgical fastener through at least one of the multiple indentations, and
     wherein each of the multiple indentations comprises an elongated slit extending from the distal edge; and
   at least one fastener connected to the holding member proximate to the proximal edge and configured to hold a sample of biocompatible material in apposition to the first side of the holding member prior to implantation of the sample of biocompatible material at an implantation site, and
   a sheet-like sample of biocompatible material having a proximal edge, a distal edge, and a general shape complementary to the general shape of the holding member,
     wherein the proximal edge of the sample of biocompatible material is detachably connected proximate to the proximal edge of the holding member and the backing member is detachably connected proximate to the distal edge of the holding member,
     wherein the holding member is configured to be detached from the sample of biocompatible material after implantation of the sample of biocompatible material at the implantation site,
     wherein the sample of biocompatible material comprises an acellular tissue matrix configured to be fastened to tissue at or proximate to an inframammary fold, and wherein the holding member is configured to hold the tissue matrix in apposition to the first side of the holding member.

2. The device of claim 1, wherein the multiple indentations are formed along the entire convex portion of the distal edge.

3. The device of claim 1, wherein each of the multiple indentations defines a rectangular form.

4. The device of claim 1, wherein the distal edge of the holding member is configured to produce a desired contour of a portion of a breast.

5. The device of claim 1, wherein the holding member is biconvex in shape.

* * * * *